(12) United States Patent
Bradshaw et al.

(10) Patent No.: US 7,061,608 B2
(45) Date of Patent: Jun. 13, 2006

(54) APPARATUS AND METHOD FOR CALIBRATION OF SPECTROPHOTOMETERS

(75) Inventors: John Thomas Bradshaw, Gorham, ME (US); Richard H. Curtis, Gorham, ME (US)

(73) Assignee: Artel, Inc., Westbrook, ME (US)

( * ) Notice: Subject to any disclaimer, the term of this patent is extended or adjusted under 35 U.S.C. 154(b) by 203 days.

(21) Appl. No.: 10/768,644

(22) Filed: Jan. 30, 2004

(65) Prior Publication Data

US 2005/0168737 A1 Aug. 4, 2005

(51) Int. Cl.
*G01J 3/42* (2006.01)
*G01J 1/10* (2006.01)

(52) U.S. Cl. .................. 356/319; 356/243.1; 356/244; 356/300

(58) Field of Classification Search ................ 356/300, 356/319, 356, 328, 243.1, 244
See application file for complete search history.

(56) References Cited

U.S. PATENT DOCUMENTS

| 4,682,890 | A | * | 7/1987 | de Macario et al. ........ 356/244 |
| 4,692,620 | A | * | 9/1987 | Rosenthal ................... 250/343 |
| 5,258,308 | A | | 11/1993 | Freeman et al. |
| 5,298,978 | A | | 3/1994 | Curtis et al. |
| 5,492,673 | A | | 2/1996 | Curtis et al. |
| 5,963,318 | A | | 10/1999 | Held |
| 6,074,614 | A | | 6/2000 | Hafeman et al. |
| 6,084,683 | A | * | 7/2000 | Bruno et al. ................ 356/446 |
| 2003/0030797 | A1 | * | 2/2003 | Palladino et al. ........ 356/243.1 |
| 2003/0107738 | A1 | | 6/2003 | Curtis |
| 2003/0160961 | A1 | * | 8/2003 | Hafeman et al. ........... 356/433 |

FOREIGN PATENT DOCUMENTS

| GB | 2131195 A | * | 6/1984 |
| WO | WO 03/079030 | | 9/2003 |

* cited by examiner

*Primary Examiner*—F. L. Evans
(74) *Attorney, Agent, or Firm*—Verrill Dana, LLP; Chris A. Caseiro; Brian J. Libby

(57) ABSTRACT

An apparatus and related method for optical calibration of spectrophotometers is described. The apparatus is a calibration plate including one or more cuvettes filled with solutions of interest. The cuvettes are sealed to prevent evaporation. The cuvettes also possess a compressible component to allow for expansion of the solution and a bubble control apparatus to ensure that the compressible component does not intersect the beam path. A piece of neutral density glass is optionally included in the apparatus to track optical changes of the solutions over time.

32 Claims, 6 Drawing Sheets

APPARATUS AND METHOD FOR CALIBRATION OF SPECTROPHOTOMETERS

CROSS-REFERENCE TO RELATED APPLICATION

The present invention relates to U.S. patent application Ser. No. 10/021,112, entitled "PHOTOMETRIC CALIBRATION OF LIQUID VOLUMES" filed Dec. 12, 2001, now U.S. Pat. No. 6,741,365 issued on May 25, 2004, and owned by a common assignee. The contents of the related application are incorporated herein by reference.

FIELD OF THE INVENTION

The present invention relates to a device and method to calibrate spectrophotometers. More particularly, the present invention is a calibration plate with one or more references of selectable absorbance characteristics.

BACKGROUND OF THE INVENTION

Many analysis methods used in biology, chemistry, biotechnology, pharmaceutical and other industrial and research laboratories require accurate measurement and/or calibration of small volumes of liquids. These small volumes can range from nanoliters to microliters. Small volumes of liquid are dispensed from liquid delivery devices, such as pipettes, either sequentially or simultaneously into one or more vessels, such as cuvettes.

In the interest of evaluating a large number of samples of liquid in a desired period of time, multiple charges of liquid samples may be dispensed into a plurality of vessels and analyzed simultaneously or sequentially. Preferably, the plurality of vessels is contained in one or more microtiter plates during testing. A microtiter plate contains a large number of individual wells and, for photometric measurements, a transparent base. Microtiter plates enable the ability to perform more research on a shorter time scale. As a result, they have become the standard analysis platform. The wide use of microtiter plates has resulted in the creation of entire classes of supporting equipment, including various types of analytical instrumentation, such as spectrophotometers capable of measuring individual wells within a plate.

Under the photometric analysis method, the liquid sample under test is contained in the sample vessel and subjected to a light beam of a spectrophotometer. The amount of light from the incident light beam that passes through the vessel and the sample to an opposing detector of the spectrophotometer is dependent upon the characteristics of the liquid sample and the beam path length. It is important that the spectrophotometer provide accurate readings to ensure the accuracy of the liquid sample evaluation.

The Beer-Lambert law defines one useful equation to determine an important characteristic of a sample. Specifically, Beer-Lambert states that the absorbance of light by a liquid sample under test equals the path length traversed by the light beam multiplied by the molar absorptivity of the chromophore in the liquid sample and the concentration of the chromophore in the liquid sample. Knowing the molar absorptivity of the chromophore, and the path length of light, the absorbance measurement provided by the spectrophotometer enables calculation of the particular concentration of the chromophore in the liquid sample. If the path length is not known, or known with sufficient accuracy, the concentration calculated will be approximate, and possibly outside a permitted error range. In addition, if the spectrophotometer is out of specification, the absorbance values obtained from the measurement will be in error and the calculated concentration also in error. It is therefore important to maintain an accurate calibration of the spectrophotometer.

There are several types of spectrophotometers used to measure sample light absorbance. The conventional spectrophotometer transmits a light beam horizontally across the sample vessel. One type of specialized spectrophotometer transmits a light beam vertically through the sample vessel. In horizontal beam spectrophotometers, specific or fixed path lengths can generally be established, as the transmission path length is a function of the fixed cross section of the sample vessel rather than the volume of the sample in the vessel. However, the light transmission and detection method associated with a horizontal beam spectrophotometer is not suitable for use with a microtiter plate arrangement because a filled microtiter plate cannot be properly inserted into the horizontal beam path.

Vertical beam spectrophotometers generally measure solution samples in microtiter plate wells. In one form, the vertical beam spectrophotometer transmits through the sample to a detector on the opposing side of the sample, either from above the sample down through it, or from below up through the sample. The path length for the sample is potentially—and likely—variable from one sample to the next in any given microtiter plate, since the path length is directly dependent upon the volume of sample solution in the well. Other factors that contribute to variations in path length are the ionic strength of the sample solution and the surface characteristics of the plate material, which together define the curvature characteristics of the solution meniscus. All of these factors result in an undefined path length and thus imprecision in vertical beam measurements. Nonetheless, vertical beam measurements are desirable in that multiple samples may be measured more quickly than is possible using a horizontal beam spectrophotometer.

For a horizontal beam spectrophotometer, a common calibration approach used to determine the optical response for a given solution on a given instrument is to either create a series of dilutions of the solution of interest, or measure the solution in different, but known path lengths. In this approach, the ability to use a known path length allows for highly accurate determinations of the optical response of a solution and direct comparison of results from one spectrophotometer to another, or from one solution to another.

One method presently used to calibrate horizontal and vertical beam spectrophotometers involves the measurement of light absorption through a known stable glass filter referred to as a Neutral Density (ND) filter. These filters are pieces of gray-tinted sheet glass that have nearly flat absorbance characteristics over a broad range of wavelengths. ND filters are commonly sent to reference laboratories for certified measurement, which provides results that are traceable to national standards. Once standardized, the ND filters are measured in the horizontal or vertical beam spectrophotometer and the absorbance results are compared to the reference laboratory results as a gauge of accuracy of the instrument.

Although this is a common calibration method, a method that relies on ND filters alone gives little or no information about various optical effects such as: 1) out of band transmission (light passing from the source through the wavelength selection device and the sample to the detector, but outside of the desired wavelength range), 2) wavelength selection accuracy, 3) bandpass of the wavelength selection device, or 4) the shape of the transmission curve of the bandpass selection device. Therefore, reliance exclusively on instrument calibration using ND filters can lead to inaccurate absorbance results, especially when comparison is made between different instruments.

One alternative method for calibrating vertical beam spectrophotometers involves the testing of samples of reference concentrations. Solutions containing different concentrations of the specific dye or chromophore are dispensed into different wells of a microtiter plate. Measurements of optical response are then conducted on the solution-filled wells. This method has several sources of error that limits its usefulness. First, the solution may not obey the Beer-Lambert law exactly, but may slightly deviate from a linear relationship between the concentration of dye and the resulting absorbance of the solution. Second, in order to provide quantitative results, highly accurate control over the amount of liquid dispensed into each well is required. Third, the exact dimensions of the wells in the microtiter plate must be known. Fourth, any meniscus present at the surface of the solution can add to the overall error since it directly affects the path length of light through the solution.

Therefore, what is needed is an apparatus and related method for calibrating vertical beam spectrophotometers. The apparatus should be configured and arranged to be compatible with the arrangement of vertical beam spectrophotometers. The apparatus and method should allow the spectrophotometer operator to account for out of band transmissions, wavelength selection accuracy, the bandpass selection characteristics of the particular spectrophotometer, and the shape of the transmission curve of the bandpass selection. Further, the apparatus and method should resolve deviations in the linear relationship between the concentration of any reference dye in a sample under test and the resulting absorbance of the sample, be independent of the sample volume used to calibrate the spectrophotometer, allow accurate control over the path length, and eliminate meniscus errors in the light beam path.

SUMMARY OF THE INVENTION

The present invention is an apparatus and related method for calibrating spectrophotometers. The apparatus is configured and arranged to be compatible with the arrangement of vertical beam spectrophotometers, but may also be used with horizontal beam spectrophotometers. The apparatus and method enable a spectrophotometer operator to account for out of band transmissions, wavelength selection accuracy, the bandpass selection characteristics of the particular spectrophotometer, and the shape of the transmission curve of the bandpass selection. Further, the apparatus and method enables resolution of deviations in the linear relationship between the concentration of any reference dye in a sample under test and the resulting absorbance of the sample. The apparatus and related method provide accurate control over the path length, independent of the sample volume used to calibrate the spectrophotometer. Finally, the present invention eliminates meniscus errors associated with vertical beam measurements. While the description of the present invention will be directed to its advantageous use in a vertical beam spectrophotometer, it may also be used to calibrate horizontal beam spectrophotometers as well.

These and other features are achieved in the present invention through the arrangement of a calibration plate having one or more sealed calibration cuvettes, each cuvette containing a solution having one or more chromophores of selectable reference concentrations. The present invention provides the operator with the ability to calibrate a vertical beam spectrophotometer at wavelengths that correspond exactly with the solutions to be tested, rather than using the broad spectral response of ND glass. For example, if a specific dye is used as an absorbance indicator in an assay, a set of solutions with increasing concentration of the specific dye may be made and inserted into the cuvettes in the calibration plate. The calibration plate is then used to calibrate the optical response of the vertical beam spectrophotometer over the expected absorbance range of the specific dye. The potential exists for incorporating more than one dye in each cuvette, so long as the multiple dyes do not significantly overlap in their absorbance responses.

The present invention provides further advantage in its stability as a standard. Specifically, by sealing a standard in a cuvette retained in the calibration plate, the present invention minimizes changes in the standard caused by its prolonged exposure to air. An expansion zone is maintained within the cuvette to allow for thermal expansion and contraction of the solution therein during any thermal cycling. The expansion zone may be established in a variety of ways, including the means to be described herein. An expansion zone isolator is preferably included in the cuvette to isolate the expansion zone from the portion of the cuvette exposed to the spectrophotometer beam. Options on the form of the isolator will be described herein.

The cuvette is oriented in the calibration plate such that it presents to the vertically aligned light beam a fixed path length through the solution. Further, that cuvette orientation displaces any meniscus from the beam path. In effect, the present invention provides a fixed path length, defined by the cross section of the cuvette, to a spectrophotometer, whether a vertical beam type or a horizontal beam type.

The calibration plate includes means for retaining one or more cuvettes. Each retained cuvette defines a test section of the plate and may include a unique chromophore solution for calibration. However, it is to be understood that a single test cuvette may be deployed in the calibration plate, and that multiple cuvettes may contain the same chromophore solutions. Each test section of the plate may be further defined by one or more transparent beam ports for the light beam to pass to and through the solution in the retained cuvette. Each port establishes a fixed path length cell based on the cuvette's cross section. The calibration plate optionally includes a test section including an ND glass filter for selectable comparison to that standard.

The calibration plate of the present invention includes one or more cuvettes that allow for insertion of solutions of interest. The solutions may be user defined and unique to the user's interests, or standardized solutions available commercially. In the later case, the filled cuvettes could be referenced to a spectrophotometer in the manufacturer's facility in the manner described in the related patent. The solution-filled cuvettes function as optical standards for calibrating the spectrophotometer response, or can be used to establish a relation between a given concentration of a solution and the absorbance exhibited. The solutions retained therein, the sealed arrangement of the cuvette(s), and the arrangement of the cuvette(s) within the calibration plate provide an effective means for spectrophotometer calibration, while avoiding the deficiencies in the vertical beam spectrophotometer calibration techniques in existence.

These and other advantages and aspects of the apparatus and method of the present invention will become apparent upon review of the following detailed description, the accompanying drawings, and the appended claims.

DESCRIPTION OF THE PREFERRED EMBODIMENTS

Figure 1:
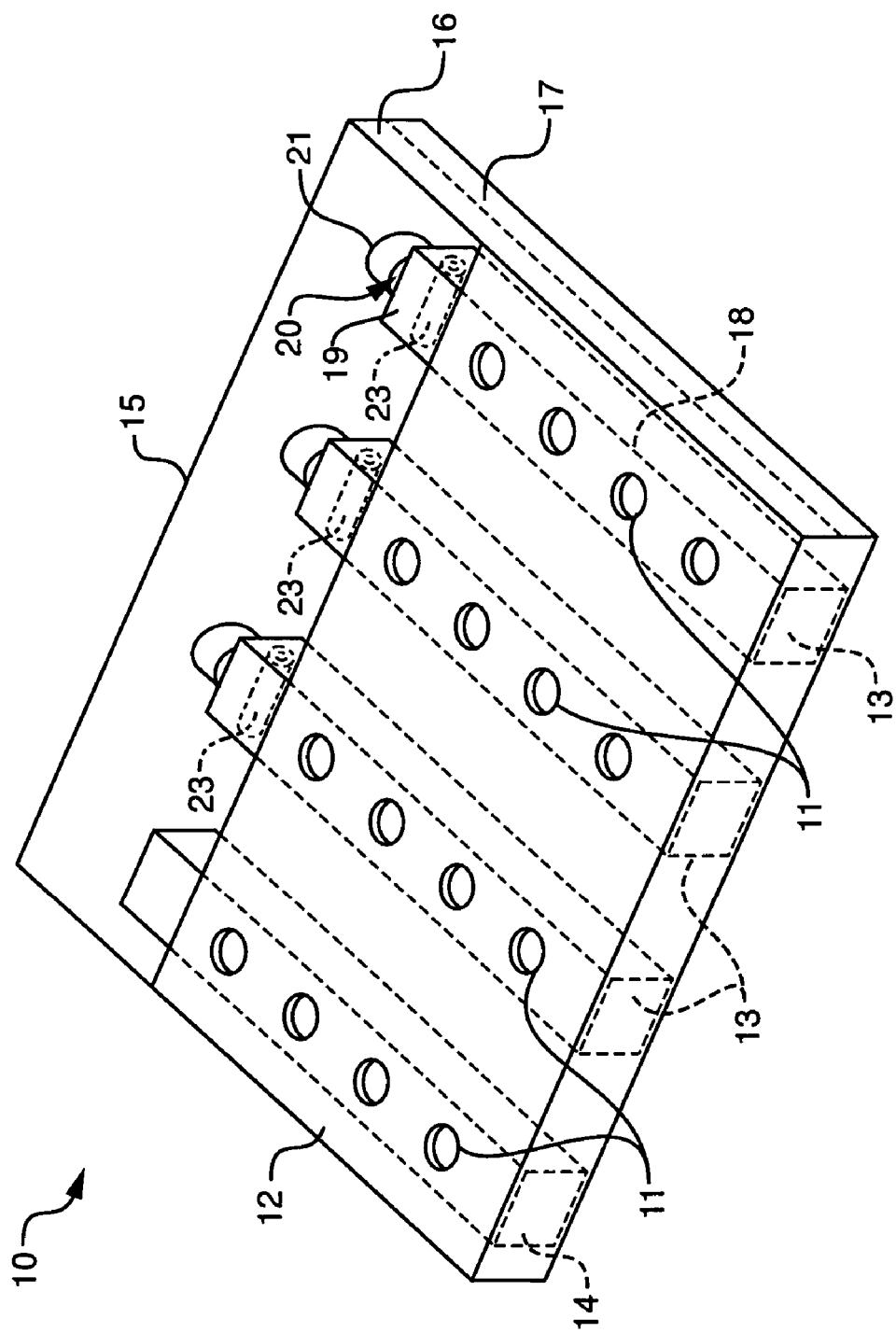
FIG. 1 is a simplified perspective view of the calibration plate of the present invention with a plurality of cuvettes and an ND glass filter shown in phantom.

A calibration plate 10 of the present invention is shown in FIG. 1. The calibration plate 10 includes a plurality of light beam ports 11 through which a light beam may pass from a top calibration plate side 12, through one or more cuvettes 13 to a back side (not shown) of the calibration plate 10. (Alternatively, the light beam may pass from the back side to the top calibration plate side 12, dependent upon the operation of the particular spectrophotometer to be calibrated.) The frame of the calibration plate 10 that defines the structure of the calibration plate 10 is preferably fabricated of a rigid opaque material including, but not limited to, a metallic material, a rigid plastic material, or a combination thereof. The frame of the calibration plate 10 is preferably fabricated of two or more sections detachably connectable to one another. The cuvettes 13, and an optional ND glass filter plate 14 are removably captured in the calibration plate 10. Specifically, they may either be inserted into, or removed from, the calibration plate at a front end 15 thereof, or by connecting/disconnecting a top calibration plate 16 to/from a bottom calibration plate 17.

With continuing reference to FIG. 1, each cuvette 13 is fabricated of a transparent material, such as glass. The cuvette 13 includes a body 18 of fixed cross sectional dimensions, an expansion allowance zone 19, a neck 20, and a head with a sealing cap 21 that seals the contents of the cuvette 13 therein. The expansion allowance zone 19 is positioned with respect the body 18 such that when the calibration plate 10 is positioned in a vertical beam spectrophotometer, the light beam ports are positioned only over the body 18 and not over the expansion allowance zone 19. Each cuvette 13 is preferably substantially filled with a liquid solution having a reference concentration or concentrations of one or more chromophores. Providing the calibration plate 10 with a plurality of cuvettes 13 allows for a range of absorbance values to be used to calibrate the optical response of a vertical beam spectrophotometer.

The cuvettes 13 are formed in a substantially rectangular shape and formed with a flanged cuvette head to enable crimp sealing thereof. Hellma International of Plainview, N.Y., is capable of providing such a cuvette arrangement. The cuvettes 13 are placed flat in their long dimension within the calibration plate 10 when the calibration plate 10 is in use to allow the calibration solution to be sealed in the cuvette 13 for long periods of time. Unlike prior calibration cuvettes, the cuvettes 13 of the present invention are sealed by sealing cap 21 to minimize or substantially eliminate gas or fluid exchanges between the solution in the cuvettes and the external atmosphere. The sealing cap 21 is a crimp top seal applied with a crimping tool in a manner well known to those skilled in the art of crimping materials onto container tops. A nonporous film is applied to the cuvette head prior to affixing the crimp top to the cuvette 13. The film is preferably a polymeric film such as Parafilm™, a plastic wrap material manufactured by Pechiney Plastic Packaging of Menasha, Wis. The crimp top itself is a layered liner fabricated of a combination of an interior nonmetallic material and an exterior metallic material. For example, Wheaton Corp. of Millville, N.J., provides a commercially available material that includes an Aluminum/Teflon/Grey Butyl combination suitable as the crimp top material. Inside the sealed cuvettes 13, the expansion allowance zone 19 includes a compressible component that may be a bubble of gas, such as air. The compressible component is established in the cuvette 13 to allow for the solution to expand/contract due to thermal fluctuations.

The compressible component must be held out of the light path defined by the ports 11, or it will adversely affect the absorbance values measured. A bubble control apparatus 23 is therefore used to hold the compressible component in place in the expansion allowance zone 19, out of the beam path near the top of the cuvette 13. While the compressible component may be displaced within the body 18 of the cuvette 13 during transport, shaking of the calibration plate 10 in any manner commonly employed in the field of liquid analysis, and the positioning of the calibration plate 10 in a vertical orientation will move the compressible component into the expansion allowance zone 19 where it is retained in place once the calibration plate 10 is returned to a horizontal orientation by the bubble control apparatus 23.

As indicated, the ND glass filter 14 is an optional component of the calibration plate 10. The ND glass filter 14 may be used to check the long-term stability of the solution filled cuvettes 13. The ND glass filter 14 is preferably a gray-tinted sheet glass, which provides a non-changing, relatively flat absorbance over large portions of the visible spectrum. Unlike its application as a calibration device in and of itself, the optional ND glass filter 14 of the present invention is used mainly to test potential degradation of the solutions in the cuvettes 13. Specifically, the operator of the spectrophotometer under calibration may track the test responses of the solution-filled cuvettes 13 versus the ND glass filter 14, rather than using the ND glass filter 14 itself to calibrate the spectrophotometer. This is accomplished by establishing a relationship between the optical response of the ND glass filter 14 at a given wavelength, and the response of a solution-filled cuvette 13 at the same wavelength. This relation may be established by the manufacturer and passed to the user, or can be established directly by the user. The relationship can be a ratio or a simple difference of the absorbance measured at a given wavelength. As the calibration plate 10 is used in the field, a comparison may be made between the ND glass filter 14/solution-filled cuvette 13 relationship measured on the date of manufacture and the relationship measured on the current day. The manufacturer or user can set tolerance limits, which will define whether one or more specific cuvettes 13 of a particular calibration plate 10 is out of specification and in need of recertification. Thus, the ND glass filter 14 is preferably optionally used as a standard reference point for checking the solution-filled cuvettes 13.

Figure 2A:
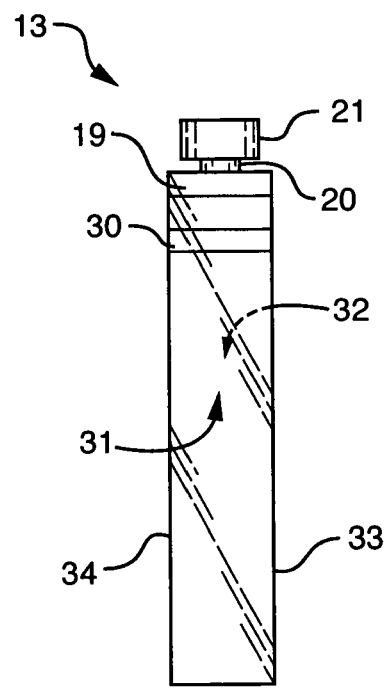
FIG. 2A is a top view of a cuvette of the present invention showing the crimp top and a first expansion isolation means.
Figure 2B:
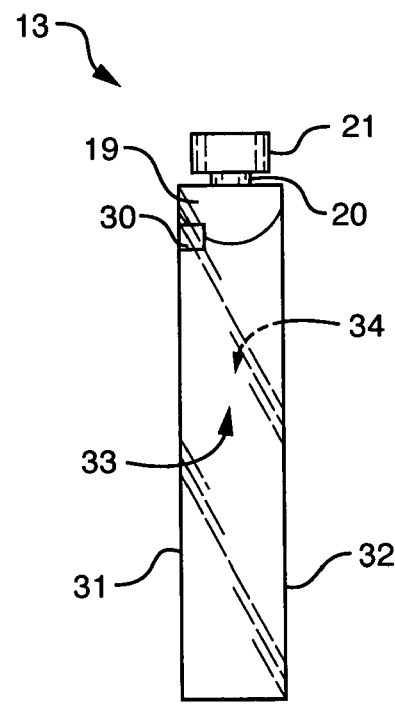
FIG. 2B is a side view of the cuvette of FIG. 2A
Figure 3A:
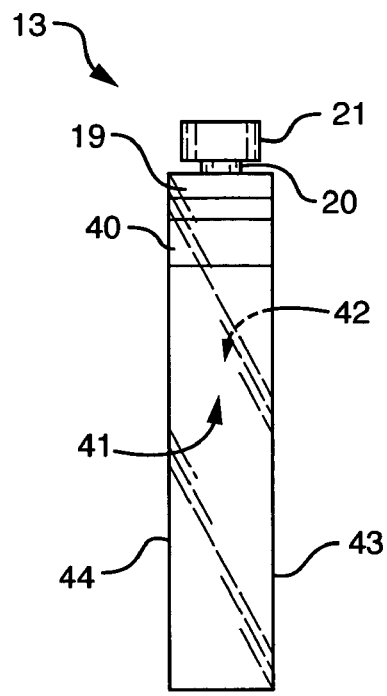
FIG. 3 is a top view of a cuvette of the present invention showing the crimp top and a second expansion isolation means.
FIG. 3B is a side view of the cuvette of FIG. 3A.
Figure 3B:
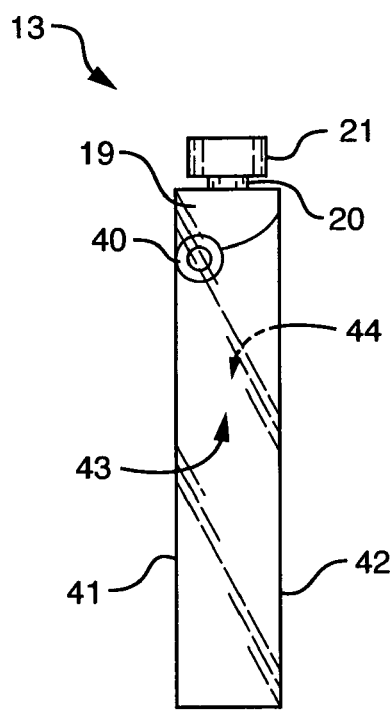
Figure 4A:
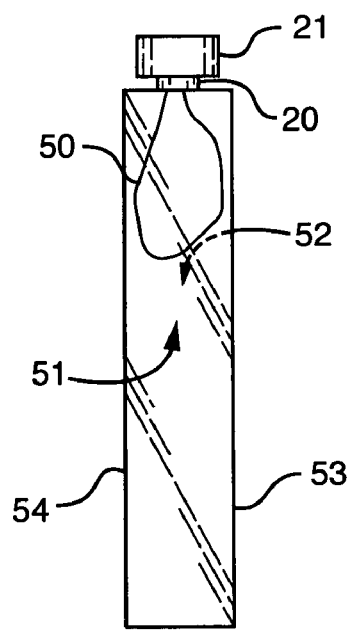
FIG. 4A is a top view of a cuvette of the present invention showing the crimp top and a third expansion isolation means.
Figure 4B:
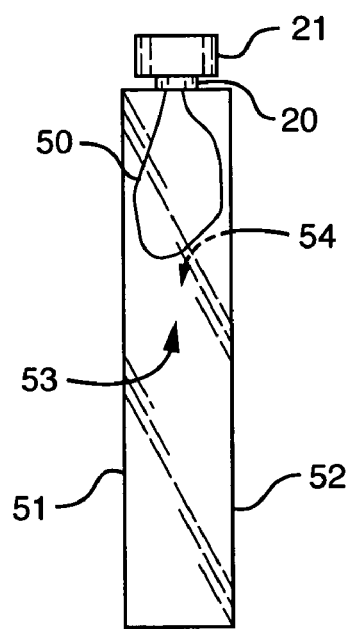
FIG. 4B is a side view of the cuvette of FIG. 4A.

As illustrated in FIGS. 2A and 2B, a first bubble control apparatus 30 is a shelf positioned adjacent to top wall 31, spaced away from back wall 32, and located between sidewalls 33 and 34 of the cuvette 13. The shelf 30, preferably fabricated of Teflon™, provides a physical barrier and holds the compressible component (bubble 19) in place mainly by surface tension. Alternatively, the shelf 30 may be fabricated of glass and fused to the interior of the cuvette 13, such as on the interior of cuvette 13 between sidewalls 33 and 34 during cuvette manufacturing. For purposes of the description of this invention, a top wall is the portion of the cuvette 13 within the top calibration plate 16 that is adjacent to the light beam ports 11 when the cuvette 13 is in position in the calibration plate 10 as shown in FIG. 1, and a bottom wall is that portion of the cuvette 13 within the bottom calibration plate 17 that is adjacent to the underside of the calibration plate when the cuvette 13 is positioned therein. All references herein to a top wall or a bottom wall of the cuvette 13 are based on this orientation. As illustrated in FIGS. 3A and 3B, a second bubble control apparatus 40 is a piece of tubing, preferably fabricated of silicone, spaced adjacent to the top wall 41, away from the bottom wall 42, and wedged into place between sidewalls 43 and 44. It too operates as a physical barrier for entrapping the compressible component (again, in this instance, bubble 19). As illustrated in FIGS. 4A and 4B, a third bubble control apparatus 50 is a bladder filled with the appropriate amount of gas to allow for solution expansion. In the device of FIGS. 4A and 4B, the compressible component is contained within the bladder 50, which extends within the cuvette 13 substantially from top wall 51 toward bottom wall 52, about from sidewall 53 to sidewall 54, and partially into neck 20. The bladder 50 is sized to prevent its passage into the cuvette body 18. Each one of these control mechanisms ensures that the compressible material will remain out of the light path during spectrophotometer calibration.

Figure 5A:
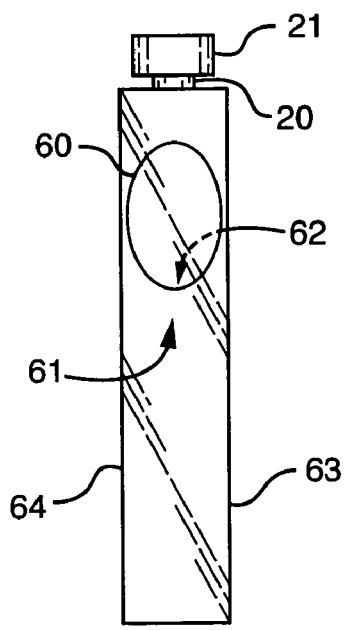
FIG. 5A is a top view of a cuvette of the present invention showing the crimp top and an optional expansion means.
Figure 5B:
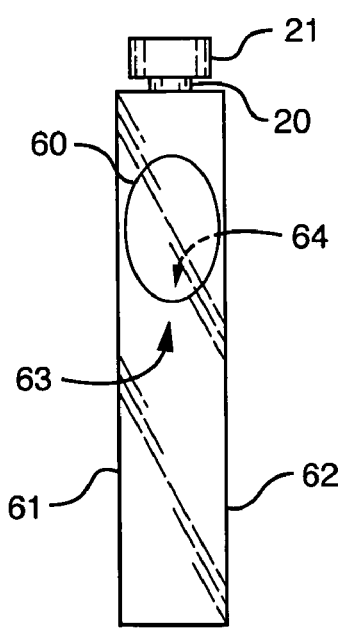
FIG. 5B is a side view of the cuvette of FIG. 5A.
Figure 6A:
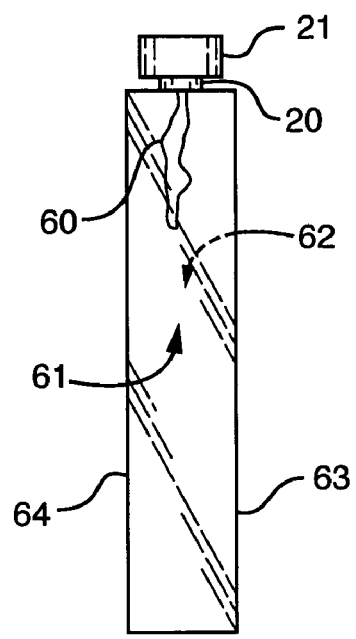
FIG. 6A is a top view of the cuvette of FIG. 5 showing the optional expansion means in a pressed form.
Figure 6B:
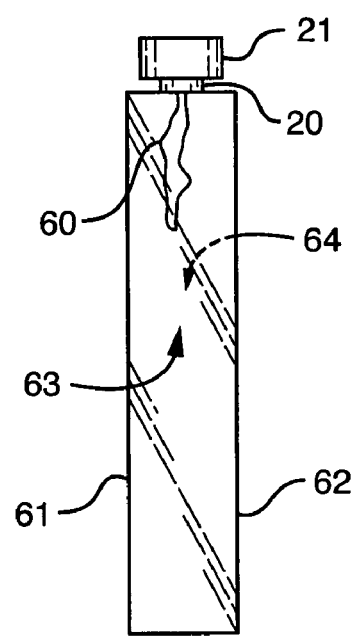
FIG. 6B is a side view of the cuvette of FIG. 6A.

A fourth bubble control apparatus 60 is shown in FIGS. 5A–5B and 6A–6B. The apparatus 60 is a porous compressible or crushable material, such as foam. The material 60 wedged between cuvette top wall 61 and bottom wall 62. It may also be spaced between sidewalls 63 and 64, or spaced away therefrom. The bubble control apparatus 60 preferably extends into a portion of the neck 20. It holds a majority of the necessary gas in its interior. Under pressure, it will either compress to a smaller overall volume and re-expand upon release of that pressure, if compressible, or it will be crushed to that smaller volume and remain that way if the material 60 is only crushable. A crushable material may be preferred for the purpose of making a rapid visual determination of solution expansion within the cuvette 13. Specifically, as shown in FIGS. 5A and 5B, under standard temperature, the solution within the cuvette 13 is of a certain volume that, in combination with the volume of the material 60, essentially fills the cuvette 13. When a change of temperature causes the solution in the cuvette 13 to expand, the material 60 is compressed, thereby reducing its volume, as shown in FIGS. 6A and 6B. At all times the path length through the cross section of the cuvette 13 remains the same. It is to be understood that any of the cuvettes 13 may include a combination of any two or more of the bubble control apparatuses described herein. For example, the shelf 30 may be used to retain the bladder 50 in place, or the compressible material 60. Alternatively, the tubing 40 may be used in place of the shelf 30 for the same purpose.

A method of calibrating a vertical-beam spectrophotometer using the calibration plate 10 includes the steps of inserting the solution-filled cuvettes 13 into the calibration plate 10, arranging the calibration plate 10 such that the compressible component is retained in the expansion allowance zone 18, and inserting the calibration plate 10 into the spectrophotometer. The cuvettes 13 are preferably filled with one or more solutions having one or more chromophores of reference absorbance characteristics and concentrations. The spectral analysis is then performed and absorbance values for the solutions in the cuvettes 13 are obtained. Those values are then compared with the reference values. The spectrophotometer operation may then be adjusted as necessary to establish a match of measured and reference absorbance values. The measurements are preferably re-run after spectrophotometer adjustment to confirm the results. The ND glass filter 14 may be used to confirm the absorbance values for the solutions in the cuvettes 13 over time as described hereinabove.

The present invention is an apparatus to calibrate the optical response of a vertical bean spectrophotometer. It allows for use of absorbance standards specific to the chromophores of interest. In effect, a chromophore commonly analyzed in assays may be used to create specific absorbance characteristics and the response thereto may be acquired using a vertical beam spectrophotometer. While the present invention has been described with particular reference to certain embodiments of the calibration plate 10 and the designs of the cuvette 13, it is to be understood that it includes all reasonable equivalents thereof as defined by the following appended claims.

What is claimed is:

1. An apparatus for calibrating a spectrophotometer, the apparatus comprising:
   a. a calibration plate having a first face, a second face, means for removably retaining therein one or more cuvettes, and one or more light beam ports from said first face through to said second face, or from said second face through to said first face; and
   b. a cuvette containing a solution, wherein the solution includes one or more chromophores.

2. The apparatus as claimed in claim 1 comprising a plurality of cuvettes retained in said means for removably retaining therein one or more cuvettes.

3. The apparatus as claimed in claim 2 wherein each of said plurality of cuvettes is filled with a solution, wherein the solution includes one or more chromophores.

4. The apparatus as claimed in claim 3 wherein the solutions in each of the plurality of cuvettes are different from one another.

5. The apparatus as claimed in claim 1 further comprising means for retaining therein a Neutral Density (ND) glass filter.

6. The apparatus as claimed in claim 5 further comprising a ND glass filter retained in said means for retaining a ND glass filter.

7. The apparatus as claimed in claim 3 wherein each of said plurality of cuvettes filled with a solution includes a top, the apparatus further comprising means for sealing said top.

8. The apparatus as claimed in claim 7 wherein said means for sealing said top includes a crimp-top seal.

9. The apparatus as claimed in claim 8 wherein said means for sealing said top includes a film disposed between said top and said crimp-top seal.

10. The apparatus as claimed in claim 2 wherein each of said plurality of cuvettes is oriented within said means to present to the spectrophotometer a fixed beam path through each of said one or more beam ports.

11. The apparatus as claimed in claim 3 wherein each of said solution-filled cuvettes includes a sealed top, an expansion allowance zone, and a compressible component therein.

12. The apparatus as claimed in claim 11 wherein said compressible component is a gas.

13. The apparatus as claimed in claim 12 wherein said gas is air.

14. The apparatus as claimed in claim 12 wherein each of said solution-filled cuvettes includes a bubble control apparatus configured and arranged to hold said gas in said expansion allowance zone when the apparatus is in use to calibrate the spectrophotometer.

15. The apparatus as claimed in claim 14 wherein said bubble control apparatus is a shelf.

16. The apparatus as claimed in claim 15 wherein said shelf is fabricated of a rigid material.

17. The apparatus as claimed in claim 16 wherein said rigid material is glass.

18. The apparatus as claimed in claim 14 wherein said bubble control apparatus is a non-metallic tube.

19. The apparatus as claimed in claim 14 wherein said bubble control apparatus is a bladder containing said gas therein.

20. The apparatus as claimed in claim 14 wherein said bubble control apparatus is a porous material containing said gas therein.

21. The apparatus as claimed in claim 14 wherein said bubble control apparatus consists of a combination of two or more of a rigid shelf, a non-metallic tube, a bladder, and a porous material.

22. A method for calibrating a spectrophotometer comprising the steps of:
  a. placing a calibration plate including one or more solution-filled cuvettes in the spectrophotometer, said calibration plate including one or more beam ports associated with each of said one or more solution-filled cuvettes, each of said one or more solution-filled cuvettes including one or more chromophores of reference light absorbance therein, each of said solution-filled cuvettes configured and arranged to present a fixed beam path to the spectrophotometer;
  b. measuring the light absorbance of each of said solution-filled cuvettes;
  c. obtaining reference light absorbance values of the one or more solution-filled cuvettes from a reference spectrophotometer; and
  d. comparing the measured light absorbance values with the reference light absorbance values.

23. The method as claimed in claim 22 wherein the calibration plate further includes a Neutral Density (ND) glass filter, the method further comprising the step of evaluating the light absorbance of each of said one or more solution-filled cuvettes over time in relation to the light absorbance of said ND glass filter.

24. The method as claimed in claim 23 wherein the step of evaluating the light absorbance of each of said one or more solution-filled cuvettes over time includes the steps of:
  a. measuring the light absorbance of the ND glass filter and one or more of said one or more solution-filled cuvettes at a first time;
  b. recording the light absorbance values of said ND glass filter and said one or more solution-filled cuvettes at said first time;
  c. measuring the light absorbance of the ND glass filter and one or more of said one or more solution-filled cuvettes at a second time; and
  d. comparing the light absorbance values from said measuring at said first time and said measuring at said second time.

25. A cuvette for calibrating a spectrophotometer, the cuvette comprising a top with a crimp seal, an expansion allowance zone, a solution including one or more chromophores, and a compressible component therein.

26. The cuvette as claimed in claim 25 wherein the compressible component is a gas.

27. The cuvette as claimed in claim 25 further comprising a non-metallic film disposed between said top and said crimp seal.

28. A cuvette having a top, the cuvette comprising a crimp-top seal to cover the top and a film disposed between the top and the crimp-top seal.

29. The cuvette as claimed in claim 28 wherein the film is a non-metallic film.

30. The cuvette as claimed in claim 28 further comprising an expansion allowance zone and a compressible component therein.

31. An apparatus for calibrating a spectrophotometer, the apparatus comprising:
  a. a calibration plate having a first face, a second face, means for removably retaining therein one or more cuvettes and a Neutral Density (ND) glass filter, and one or more light beam ports from said first face through to said second face, or from said second face through to said first face;
  b. one or more cuvettes placeable in the means for removably retaining, wherein each of the one or more cuvettes is arranged to contain a solution having one or more chromophores; and
  c. a ND glass filter placeable in the means for removably retaining.

32. The apparatus as claimed in claim 31 wherein the calibration plate is formed of a top calibration plate and a bottom calibration plate, wherein the means for removably retaining therein the one or more cuvettes and the ND glass filter is the connecting/disconnecting of the top calibration plate and the bottom calibration plate to insert or remove the one or more cuvettes and/or the ND glass filter.

* * * * *